United States Patent [19]
Gallagher

[11] Patent Number: 5,670,709
[45] Date of Patent: Sep. 23, 1997

[54] TRANSDUCER FOR THE MEASUREMENT OF ATTRIBUTES OF FLOWABLE MEDIA

[76] Inventor: John G. Gallagher, 77 Town Street, Malton, North Yorkshire, England, YO17 9HB

[21] Appl. No.: 448,362

[22] PCT Filed: Nov. 29, 1993

[86] PCT No.: PCT/GB93/02453

§ 371 Date: Jul. 20, 1995

§ 102(e) Date: Jul. 20, 1995

[87] PCT Pub. No.: WO94/14047

PCT Pub. Date: Jun. 23, 1994

[30] Foreign Application Priority Data

Dec. 12, 1992 [GB] United Kingdom .................. 9225983

[51] Int. Cl.[6] ........................................... G01N 11/10
[52] U.S. Cl. ................................. 73/54.24; 73/32 A
[58] Field of Search ...................... 73/54.23, 54.24, 73/54.25, 54.26, 54.27, 54.41, 32 A

[56] References Cited

U.S. PATENT DOCUMENTS

| | | | |
|---|---|---|---|
| 2,142,854 | 1/1939 | La Pierre | 73/54.25 |
| 3,062,040 | 11/1962 | McKennell et al. | 73/54.24 |
| 3,282,084 | 11/1966 | Banks | 73/32 |
| 3,349,604 | 10/1967 | Banks | 73/54.24 |
| 3,525,252 | 8/1970 | Kocatas | 73/54.23 |
| 3,625,058 | 12/1971 | Endress et al. | |
| 4,547,691 | 10/1985 | Valdois et al. | 310/361 |
| 4,740,726 | 4/1988 | Umezawa | |
| 4,920,787 | 5/1990 | Dual et al. | 73/54.41 |
| 5,317,908 | 6/1994 | Fitzgerald et al. | 73/54.25 |
| 5,323,638 | 6/1994 | Langdon | 73/54.27 |

FOREIGN PATENT DOCUMENTS

| | | |
|---|---|---|
| 0 282 251 | 9/1988 | European Pat. Off. |
| 0 564 682 A1 | 5/1993 | European Pat. Off. |
| 2 039 369 | 3/1983 | United Kingdom |
| 2 202 944 | 7/1991 | United Kingdom |
| WO83/01307 | 4/1983 | WIPO |

*Primary Examiner*—Hezron E. Williams
*Assistant Examiner*—Jay L. Politzer
*Attorney, Agent, or Firm*—Nixon & Vanderhye P.C.

[57] ABSTRACT

A transducer measures density, viscosity, flowrate or suchlike of fluids or flowable solids using a resonator having two vibratile beam elements, one of which is disposed coaxially within the other. The outer element may be a closed tube which forms a chamber around the inner element. A drive and sensor may be disposed on a base which provides a common root for the beam elements.

20 Claims, 1 Drawing Sheet

TRANSDUCER FOR THE MEASUREMENT OF ATTRIBUTES OF FLOWABLE MEDIA

BACKGROUND OF THE INVENTION

The present invention relates to transducers for the measurement of attributes of flowable media, for example the density, viscosity, mass flow or the level of a fluid or a flowable solid.

RELATED ART

It is known for example from GB-B-2202944 to provide a transducer which essentially comprises a resonator in the general form of a tuning fork for the measurement of attributes of flowable media. The fork is usually constructed from two parallel beam elements of which the longitudinal axes are laterally spaced apart. These beam elements may be tubes which contain the fluid or tines which are immersed in the medium. When tubes are used there is usually a limitation in the size of the bore, limiting the flowrate, and it is usually necessary to provide some means for directing the medium through the tubes, for example a pump. If the device is adapted for insertion into the flowable medium, there is no need for ancillary equipment such as pipe fittings and the transducer can usually be made smaller and easier to install. However, devices employing a pair of tines are susceptible to error or inconvenience arising from the entrapment of debris between the tines, such debris affecting the desired vibration and accordingly the accuracy of measurement.

SUMMARY OF THE INVENTION

The invention is generally concerned with the provision of improved and versatile transducers and more particularly an improved transducer which reduces some of the disadvantages associated with a device comprising a pair of spaced apart tines.

The present invention is based on a structure which in preferred forms can be described as a coaxial resonator, for example a resonator composed of two vibratile beam elements having a common base or root, a first of the beam elements being disposed at least partially within the other. In the manner of a tuning fork, when one beam element, for example the outer beam element, is displaced at its distal end, it creates at its base or root a torque moment, which is equalized by the sympathetic movement of the other beam element, there being practically no net displacement at the common base or root. The structure provides a highly efficient vibrating system, having a natural frequency dependent on the physical characteristics, such as the mass and stiffness of the beam elements.

BRIEF DESCRIPTION OF THE DRAWINGS

Various other features and aspects of the invention are more conveniently described with the aid of the accompanying drawings.

DETAILED DESCRIPTION OF EXEMPLARY EMBODIMENTS

Figure 1:
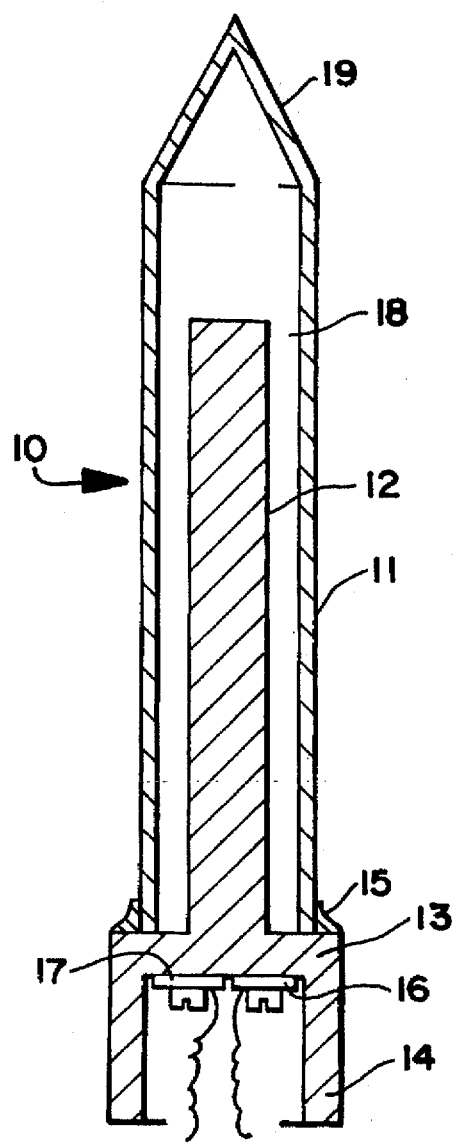
FIG. 1 illustrates in simplified form one embodiment of a transducer according to the invention.

FIG. 1 illustrates by way of example one embodiment of a transducer according to the invention. This transducer 10 is in the form of a coaxial resonator and comprises two vibratile beam elements, one located inside the other. The outer beam element 11 in this example comprises a tube and the inner element 12 is in the form of a substantially solid tine. Both elements 11 and 12 are either integral with or secured to a base or root 13.

Like a tuning fork, when one beam element, for example the element 11, is displaced or vibrated, it vibrates in the manner of a cantilever beam and accordingly creates at its base or root a torque moment, which is equalized by the sympathetic movement of the other beam element to create practically no resulting displacement at the base or root. The result is an efficient vibrating system with a natural frequency dependent on the mass and stiffness of the elements 11 and 12.

In the present embodiment, the base 13 has a rearwardly extending flange 14 defining a well or partial enclosure wherein an appropriate means for inducing vibration in the resonant structure and for sensing either displacement, strain or other characteristic of the resonant structure may be disposed. This is not the only possible location of such drive means and sensing means but the location specified here is particularly convenient for the structure shown in FIG. 1. In this embodiment the drive means is constituted by a piezoelectric plate 16 attached to the underside of the base 13 which provides the common support for the vibrating beam elements and the pickup or sensing means is likewise constituted by a piezoelectric plate 17 similarly disposed on the underside of the base 13.

In the present embodiment, the outer element is closed at its distal end by a nose cone 19. Accordingly, when the transducer is inserted into a fluid, only the external surface of the outer element will be in contact with the fluid. The outer element may therefore be a simple, closed cylinder, having a low propensity for obstructing the flow, resisting insertion or for the entrapment of debris. In such an embodiment, since fluid is not permitted within the chamber 18 inside the outer element, the inner element 12 is free to vibrate without any impedance by the fluid.

When immersed into a fluid or flowable solid, the structure is still capable of acting as a resonator, but the resonant characteristics may be modified by the medium in a variety of ways.

First, as the outer element is displaced during the execution of its natural vibrations, it displaces fluid having a mass proportional to the fluid density. This displacement increases the effective mass of the outer element, resulting in a change of resonant frequency of the transducer. By measurement of this resonant frequency the density of the surrounding fluid may be determined.

Second, as the outer element is displaced during the execution of natural vibration, its surface shears through the fluid, creating a drag force due to viscosity in the outer element. This results in a loss of energy from the vibrating system, manifested by a decrease in the Q (quality factor) of the resonant peak. By measurement of that quality factor, the viscosity of the surrounding fluid may be determined.

Third, if the transducer is so oriented that the longitudinal axis of the outer element is parallel to the flow of the fluid, the transducer causes periodic disturbances normal to the flowing fluid, creating a coriolis force across the length of the tube, in proportion to the mass flowrate. This coriolis force can be measured as a variation in oscillatory phase of the outer element, the measurement being capable of providing an indication of the coriolis acceleration and accordingly the mass flowrate.

Fourth, if the outer element is only partially covered by the external fluid, it will vibrate at a frequency proportional to the amount of covering fluid in a fluid density. The fluid density can be established from a second, fully covered, vibrating element, so that the resonant frequency is a function of fluid cover or level. The outer element might be short, such as only ten centimeters, or long, such as ten meters, to embrace the variation required to measure different levels.

In a similar way to that just described, the transducer may be used as a level switch. The frequency of vibration in air or a vacuum can be established. The presence of small quantities of material on the surface of the outer element can result in a change of the natural frequency of vibration. By monitoring the resonant frequency of the apparatus, one may indicate the presence or absence of material. This configuration of the device is applicable to the detection of non-fluid matter such as particulate solids.

The resonant structure may be driven into sustained vibration from a periodic energy source in the appropriate phase and frequency relationships with a mechanical displacement of the vibrating elements. The drive means may be electromagnetic, acoustic, or capacitative, or operate by deformation of piezoelectric devices bonded at some appropriate point, as shown in FIG. 1, and driven using a periodically varying electrical signal. The vibration may be sensed by a variety of techniques which create an electrical signal in response to a displacement or strain at a mechanically efficient point in the apparatus. As noted in the foregoing, FIG. 1 illustrates the use of a piezoelectric element as a vibration sensor at the base of the apparatus, but many other forms of sensor maybe employed.

The structure can be driven into continuous oscillation by the use of a gain limiting amplifier and the suitable matching of phase between drive and pickup transducers. Feedback from the sensing transducer may be used for this purpose.

Further embodiments of the invention may employ inner and outer elements driven at higher cantilever modes of vibration and combinations thereof. For example, the outer element may be tuned to vibrate at its second or third mode whereas the inner element can be maintained at a fundamental mode. The selection of modes may be based on a choice of mass or stiffness characteristics of the two elements so that there is no resultant displacement at the base of the apparatus or otherwise. Vibration of the outer element at a higher mode can create greater sensitivity of measurement and improve immunity to variation in mounting conditions at the base.

Figure 2:
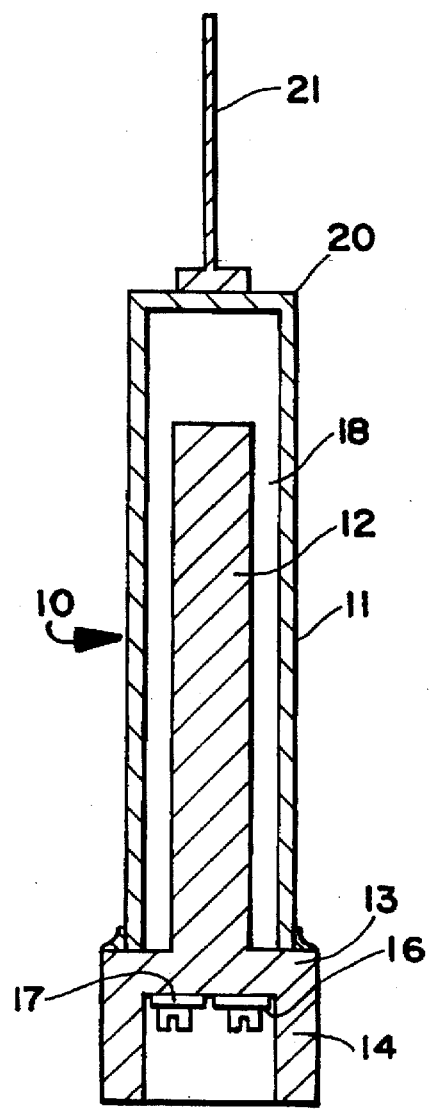
FIG. 2 illustrates a second embodiment of a transducer according to the invention.

FIG. 2 illustrates an embodiment similar to that shown in FIG. 1, using a fixed or removable extension to the outer element. Those parts of FIG. 2 which are common to the embodiment of FIG. 1 are denoted by the same reference numbers are will not be described again. In the embodiment of FIG. 2, the outer tube 11 has a flat end cap 20, which carries a vane 21 constituting an extension to the vibrating structure.

If the vane 21 were disposed in a plane normal to the vibration, it would increase the surface area disturbing the fluid and therefore improve the sensitivity of density measurement. If the vane were disposed at right angles to the position shown, so that it were parallel to the plane of vibration, it would increase the shear surface and thereby improve sensitivity in the measurement of viscosity.

The vibrating elements may be elliptical, square, or polygonic in cross-section in accordance with different effects of the section on the measurement of different attributes.

Further embodiments of the invention may include a port, for example in the base 13, allowing fluid to flow into the chamber 18 between the inner and outer elements to equalize the pressure on the outer element and reduce any pressure stress thereon.

Further modifications to the disclosed embodiments are feasible. For example, the transducer may be incorporated into a system having more than two elements. It may be advantageous to mount the base on a semi-rigid bellows or other means which provides at least some mechanical decoupling between the transducer and a structure to which it may be attached.

I claim:

1. Apparatus for the measurement of attributes of flowable media including a resonator comprising:

a first and a second vibratile cantilever beam element, each extending from a common root and forming a vibrating system with a natural frequency dependent on the mass and stiffness of said first and second vibratile cantilever beam elements;

the torque moments of said first and second vibratile cantilever beam elements on said common root being practically equal;

said first vibratile cantilever beam element including a tube defining a chamber; and said second vibratile cantilever beam element being disposed within said chamber.

2. Apparatus as in claim 1 wherein:

said chamber is a closed chamber whereby the said second vibratile cantilever beam element vibrates without impedance by the flowable medium.

3. Apparatus as in claim 1 wherein:

transducers for inducing vibration of said first and second vibratile cantilever beam elements and for sensing at least one attribute of vibration of said first and second vibratile cantilever beam elements are disposed on the said common root.

4. Apparatus as in claim 3 wherein:

said transducers are piezoelectric transducers.

5. Apparatus as in claim 1 wherein:

the longitudinal axes of said first and second vibratile cantilever beam elements are coaxial.

6. Apparatus as in claim 1 wherein:

said first vibratile cantilever beam element carries a longitudinal extension in the form of a vane.

7. Apparatus for the measurement of attributes of flowable media including a resonator comprising:

first and second vibratile cantilever beam elements having a common root and forming a vibrating system with a natural frequency dependent on the mass and stiffness of said first and second vibratile cantilever beam elements;

the torque moments of the first and second vibratile cantilever beam elements on the common root being practically equal; and said first and second cantilever beam elements being an outer element in the form of a tube and an inner element in the form of a solid tine disposed within the outer element.

8. Apparatus as in claim 7 wherein:

said outer element defines a closed chamber around said inner element, whereby said inner element vibrates without impedance by the flowable medium.

9. Apparatus as in claim 8 wherein:

transducers for inducing vibration of said first and second vibratile cantilever beam elements and for sensing at least one attribute of vibration of said first and second vibratile cantilever beam elements are disposed on the said common root.

10. Apparatus for the measurement of attributes of flowable media including a resonator comprising:

first and second vibratile cantilever beam elements having a common root;

said first vibratile cantilever beam element being a tube defining a chamber around said second vibratile cantilever beam inner element; and a transducer disposed on the said common root for inducing vibration of said first and second vibratile cantilever beam elements.

11. Apparatus as in claim 10 and further comprising:

a transducer disposed on the common root for sensing at least one attribute of vibration of said first and second cantilever beam elements.

12. Apparatus as in claim 10 wherein:

said chamber is a closed chamber whereby said second vibratile cantilever beam element vibrates without impedance by the flowable medium.

13. Apparatus as in claim 1 wherein there is practically no net vibration at said common root.

14. Apparatus as in claim 7 wherein there is practically no net vibration at said common root.

15. Apparatus as in claim 10 wherein there is practically no net vibration at said common root.

16. A resonator for measuring the attributes of flowable media disposed thereabout, said resonator comprising:

a base;

a first vibratory element affixed at one end to said base;

a second vibratory element also affixed at one end to said base;

said first vibratory element being disposed within said second vibratory element without contact.

17. A resonator as in claim 16 further comprising vibratory driving means disposed to simultaneously vibrate both said vibratory elements at a resonant vibrational node.

18. A resonator as in claim 17 wherein said vibratory driving means is affixed to said base.

19. A resonator as in claim 16 wherein said second vibratory element encloses said first vibratory element within a closed chamber.

20. A resonator as in claim 16 further comprising a projection element affixed to said second vibratory element at a predetermined orientation so as to interact with said flowable media and thereby change its vibratory properties.

* * * * *